United States Patent
Rouet et al.

(10) Patent No.: US 11,877,893 B2
(45) Date of Patent: Jan. 23, 2024

(54) PROVIDING A THREE DIMENSIONAL ULTRASOUND IMAGE

(71) Applicant: KONINKLIJKE PHILIPS N.V., Eindhoven (NL)

(72) Inventors: Laurence Rouet, Paris (FR); Cecile Dufour, Paris (FR); Robert Randall Entrekin, Kirkland, WA (US); Gary Cheng-How Ng, Redmond, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 32 days.

(21) Appl. No.: 16/975,766

(22) PCT Filed: Feb. 25, 2019

(86) PCT No.: PCT/EP2019/054502
§ 371 (c)(1),
(2) Date: Aug. 26, 2020

(87) PCT Pub. No.: WO2019/162477
PCT Pub. Date: Aug. 29, 2019

(65) Prior Publication Data
US 2020/0397407 A1    Dec. 24, 2020

(30) Foreign Application Priority Data
Feb. 26, 2018    (EP) .................... 18290014

(51) Int. Cl.
*A61B 8/00* (2006.01)
*A61B 8/08* (2006.01)
*A61B 8/06* (2006.01)

(52) U.S. Cl.
CPC .............. *A61B 8/466* (2013.01); *A61B 8/06* (2013.01); *A61B 8/085* (2013.01); *A61B 8/0891* (2013.01);
(Continued)

(58) Field of Classification Search
CPC .......... A61B 8/466; A61B 8/06; A61B 8/085; A61B 8/0891; A61B 8/463; A61B 8/469; A61B 8/483; A61B 8/5207; A61B 8/4254
See application file for complete search history.

(56) References Cited

U.S. PATENT DOCUMENTS

| 6,443,894 B1 | 9/2002 | Sumanaweera et al. |
| 2007/0259158 A1 | 11/2007 | Friedman et al. |
(Continued)

FOREIGN PATENT DOCUMENTS

| DE | 102016105690 A1 | 10/2016 |
| JP | 2017170131 A | 9/2017 |
(Continued)

OTHER PUBLICATIONS

International Search Report and Written Opinion for International Application No. PCT/EP2019/054502, filed Feb. 25, 2019, 14 pages.

*Primary Examiner* — Baisakhi Roy
*Assistant Examiner* — Kaitlyn E Sebastian

(57) ABSTRACT

A method and processing system for providing a three-dimensional, 3D, ultrasound image along with an additional ultrasound acquisition. A location of the additional ultrasound acquisition with respect to the three-dimensional ultrasound image is determined or obtained. After obtaining the 3D ultrasound image and the additional ultrasound acquisition, initial display data is for display of only the 3D ultrasound image. In response to a user input, second display data is generated for displaying both the 3D ultrasound image and the additional ultrasound acquisition. The display of the additional ultrasound acquisition is based on the location of the additional ultrasound acquisition with respect to the three-dimensional ultrasound image.

20 Claims, 4 Drawing Sheets

(52) U.S. Cl.
CPC .............. *A61B 8/463* (2013.01); *A61B 8/469* (2013.01); *A61B 8/483* (2013.01); *A61B 8/5207* (2013.01)

(56) References Cited

U.S. PATENT DOCUMENTS

| | | |
|---|---|---|
| 2010/0191114 A1 | 7/2010 | Hyun et al. |
| 2011/0060223 A1* | 3/2011 | Kim ................ A61B 8/469 600/443 |
| 2013/0339891 A1 | 12/2013 | Blumenberg et al. |
| 2015/0182191 A1 | 7/2015 | Caluser et al. |
| 2015/0190120 A1* | 7/2015 | Huang ............... A61B 8/485 600/438 |
| 2015/0209013 A1* | 7/2015 | Tsymbalenko ...... G01S 7/52071 600/440 |
| 2015/0213597 A1* | 7/2015 | Oh ..................... G06T 15/00 382/131 |
| 2016/0287214 A1 | 10/2016 | Ralovich et al. |
| 2017/0086780 A1* | 3/2017 | Sokulin ............... A61B 8/065 |
| 2017/0238907 A1 | 8/2017 | Kommu CHS |

FOREIGN PATENT DOCUMENTS

| | | | |
|---|---|---|---|
| WO | 2017076758 A1 | | 5/2017 |
| WO | WO2017076758 | * | 5/2017 |
| WO | 2017211910 A1 | | 12/2017 |

\* cited by examiner

US 11,877,893 B2

PROVIDING A THREE DIMENSIONAL ULTRASOUND IMAGE

RELATED APPLICATIONS

This application is the U.S. National Phase application under 35 U.S.C. § 371 of International Application No. PCT/EP2019/054502, filed on Feb. 25, 2019, which claims the benefit of and priority to European Application No. 18290014.2, filed Feb. 26, 2018. These applications are incorporated by reference herein.

FIELD OF THE INVENTION

This invention relates to the field of ultrasound imaging, and in particular to the field of three-dimensional ultrasound imaging systems.

BACKGROUND OF THE INVENTION

Ultrasound imaging is increasingly being employed in a variety of different applications. It is important to provide a user with sufficient information about the subject being scanned, in order to accurately assess a condition of a subject. This is especially the case when the subject in question is a patient undergoing a medical ultrasound scan.

Some ultrasound imaging systems comprise an ultrasound probe and an ultrasound probe tracker, adapted to track a location of the ultrasound probe. Ultrasound probes are usually adapted to be held by a clinician or other user of the ultrasound imaging system.

Ultrasound probes may comprise a capacitive micromachined ultrasonic transducer (CMUT) transducer array for transmitting ultrasound waves and receiving echo information. The transducer array may alternatively comprise piezoelectric transducers formed of materials such as lead zirconate titanate (PZT) or polyvinylidene fluoride (PVDF). The transducer array may comprise a two-dimensional array of transducers capable of scanning in a 2D plane or in three dimensions for 3D imaging. In another example, the transducer array may be a 1D array.

Known ultrasound probe trackers include electro-magnetic or optical tracking systems and transducer-based tracking systems.

Methods that generate a three-dimensional (3D) ultrasound image have been proposed. 3D ultrasound images have been shown to significantly improve a user's understanding of an imaged volume. Typically, to capture a 3D ultrasound image, the ultrasound probe captures a series of 2D ultrasound images and the ultrasound probe tracker identifies a location (of the probe) at which each image is captured. The captured 2D ultrasound images are stacked, based on their respective locations of capture, to form a 3D image of the imaged volume.

WO 2017/076758 A1 discloses an ultrasound system that provides an ultrasound image of a volumetric region. A region of interest within the volumetric region may be imaged using a higher frequency beam than the remainder of the volumetric region to thereby control an image quality of the region of interest.

SUMMARY OF THE INVENTION

The invention is defined by the claims.

Embodiments in accordance with examples of the invention provide a method of providing a three-dimensional, 3D, ultrasound image along with an additional ultrasound acquisition, the method comprising: obtaining a 3D ultrasound image of a volume from an ultrasound imaging system comprising an ultrasound probe and an ultrasound probe tracker; obtaining, from the ultrasound imaging system, an additional ultrasound acquisition of a portion of interest of the volume; identifying a location of the additional ultrasound acquisition relative to the 3D ultrasound image; and after the steps of obtaining the 3D ultrasound image and obtaining the additional ultrasound acquisition: generating first display data for display of the 3D ultrasound image; receiving a first user input; and in response to the first user input, generating second display data for display of the 3D ultrasound image and the additional ultrasound acquisition, with the display of the additional ultrasound acquisition being based on the location of the additional ultrasound acquisition.

Thus, initial display data may be for display of the 3D ultrasound image alone (and not for display of the additional ultrasound acquisition). In response to a first user input, the display data may be modified for display of the additional ultrasound acquisition as well as the 3D ultrasound image. Thus, data for display of the additional ultrasound acquisition is only included in the display data in response to a user input.

The 3D ultrasound image and the additional ultrasound acquisition(s) are obtained before the display data is generated. Thus, the proposed method provides a concept for improved manipulation of previously captured ultrasound data.

The display of the additional ultrasound acquisition in the (second) display data is dependent upon a relative location of the region imaged by the additional ultrasound acquisition with respect to the 3D ultrasound image.

The present invention relies on a concept of determining or otherwise identifying a relative location of an ultrasound acquisition within a 3D ultrasound image. This can be used to provide useful information to a clinician that helps them to contextualize the position of the ultrasound acquisition. The proposed concept therefore advantageously increases a user's cognizance of information output by an ultrasound imaging system.

In the proposed embodiments, a location of a region of interest, which is represented by the additional ultrasound acquisition, within the 3D ultrasound image is identified and used to define a display of the additional ultrasound acquisition in the second display data.

The display data may be used or processed by an ultrasound image display, e.g. comprising a monitor, in order to display the 3D ultrasound image and the additional ultrasound acquisition. The display of the additional ultrasound acquisition is dependent upon a user input. The additional ultrasound acquisition may be a two-dimensional ultrasound image, video or cine loop.

This reduces an amount of memory or processing power required to provide display data, as the user may not require the additional ultrasound acquisition to be initially displayed. Only providing the additional ultrasound acquisition in response to a user input thereby reduces a number of memory accesses required to provide a user with a relevant ultrasound acquisition. The effect of the memory reduction increases with the number of additional ultrasound acquisitions.

In some examples, the first display data is for display of the 3D ultrasound image and a user-selectable marker, the display location of the user-selectable marker being based on the location of the additional ultrasound acquisition; and the step of receiving a first user input comprises receiving a first user input in response to the user selecting the user-selectable marker.

Thus, there is proposed a concept of only displaying an additional ultrasound acquisition when (i.e. in response to) a user selects a marker that has been provided at the location of the additional ultrasound acquisition on the 3D ultrasound image.

Providing a user-selectable marker permits a user to search and retrieve stored ultrasound acquisitions more efficiently. Displaying an ultrasound acquisition only in response to selection of a corresponding marker provides a user with a simultaneous overview of the presence and availability of various ultrasound acquisitions (by way of multiple markers), and increases a user's cognizance of the total amount of information available. There is also a reduction in an amount of memory and processing power, including number of memory accesses, required to provide a user with relevant ultrasound acquisitions, as an ultrasound acquisition need only be retrieved (e.g. from a database) when a corresponding marker is selected by a user.

Moreover, in the context of a clinical analysis of a 3D ultrasound image, provision of a marker at the location of an ultrasound acquisition reduces a likelihood of clinician error, and reduces the risk of a clinician misunderstanding, misidentifying or incorrectly locating the ultrasound acquisition or portions imaged by the ultrasound acquisition, which could increase subject risk. By way of example, if a location of a tumor is misidentified by a clinician, this could lead to unnecessary or harmful treatment of the subject at an incorrect location.

Some embodiments comprise a step of determining an orientation of the additional ultrasound acquisition with respect to the 3D ultrasound image, wherein the display of the additional ultrasound acquisition (in the second display data) is based on the determined orientation of the additional ultrasound acquisition.

Embodiments therefore propose to adjust display data so that the displayed ultrasound acquisition is appropriately oriented with respect to the 3D ultrasound image. This provides additional information to a user, and improves their understanding of the relevance of a displayed ultrasound acquisition. The orientation permits a user to more precisely understand a location of the ultrasound acquisition with respect to the 3D ultrasound image. This leads to a significant reduction in user error.

In some examples, there is a step of determining how the additional ultrasound acquisition overlays the 3D ultrasound image based on the identified location; wherein the step of generating the display data comprises generating (second) display data for display of the 3D ultrasound image with the additional ultrasound acquisition overlaying the 3D ultrasound image at the identified location.

Thus, a display (based on the display data) of the additional ultrasound acquisition may overlay a corresponding portion of the displayed 3D image. In particular, if a location and optionally orientation of the additional ultrasound acquisition is known with respect to the 3D ultrasound image, the ultrasound acquisition can be appropriately displayed to overlay the 3D ultrasound image.

Embodiments allow more accurate and relevant displaying of an image. Overlaying the additional ultrasound acquisition on the corresponding portion of the 3D image reduces an amount of information displayed to a user, as the relevant portion of the 3D image will be replaced by the additional ultrasound acquisition, solving a problem of how to integrate an additional ultrasound acquisition within a 3D image. For example, a slice or segment of the 3D image may be replaced by a 2D ultrasound image/video (examples of an additional ultrasound acquisition) at that location. This allows additional information to be provided (e.g. a higher resolution 2D image or a blood flow depicted in color) whilst allowing a user to more efficiently identify a location and relevance of the additional ultrasound acquisition and minimizing an amount of data displayed.

Preferably, the step of identifying a location of the additional ultrasound acquisition comprises obtaining the location from the ultrasound probe tracker.

This increases an accuracy and precision of determining the relative location of the additional ultrasound acquisition, as the 3D ultrasound image is generated from the same ultrasound probe tracker.

In some examples, the step of identifying a location of the additional ultrasound acquisition comprises receiving another user input indicating a location of the additional ultrasound acquisition with respect to the 3D ultrasound image.

This allows a user to define a location of the additional ultrasound acquisition within the 3D ultrasound image. This may be exploited, for example, to provide additional information about the 3D ultrasound image.

By way of example, a user may extract a portion of the 3D ultrasound image to form the additional ultrasound acquisition, the location of the extracted portion being the location of the additional ultrasound acquisition. This advantageously allows a user to provide or label particular sections of the 3D ultrasound image for later review.

In some embodiments, the method comprises steps of: obtaining, from the ultrasound imaging system, a plurality of additional ultrasound acquisitions of different portions of interest of the volume; and identifying a location of each additional ultrasound acquisition relative to the 3D ultrasound image; wherein the step of generating the second display data comprises generating second display data for display of the 3D ultrasound image and at least one of the plurality of additional ultrasound acquisitions by a 3D ultrasound image display, with the display of the least one additional ultrasound acquisition being based on the respective locations of each at least one additional ultrasound acquisition.

Thus, more than one additional ultrasound acquisition may be obtained, where the second display data includes data for display of at least one of these additional ultrasound acquisitions. This enables a selection of ultrasound acquisitions to be displayed to a user, increasing their cognizance of information.

The step of generating second display data may comprise generating display data for display of the 3D ultrasound image and sequential display of each additional ultrasound acquisition, with the sequential display of each additional ultrasound acquisition being based on the respective locations of each of the additional ultrasound acquisitions.

Thus, a plurality of additional ultrasound acquisitions can be obtained and display data sequentially generated which causes the ultrasound acquisitions to be displayed sequentially, based on the relative location of the ultrasound acquisitions with respect to the 3D ultrasound image.

Sequentially displaying the additional ultrasound acquisitions can help improve a user's understanding of the ultrasound imaging process, preventing information overload to the user. Sequential display also reduces a processing power required to display the additional ultrasound acquisition, as they need not be displayed simultaneously.

In some other embodiments, the step of generating second display data may comprise generating display data for display of the 3D ultrasound image and sequential display of each additional ultrasound acquisition, with the sequential display of each additional ultrasound acquisition being based on the respective time at which each additional ultrasound acquisitions was captured by the ultrasound imaging system.

Thus, there is proposed a concept of sequentially displaying the ultrasound acquisitions based on a time at which each ultrasound acquisition was captured.

This advantageously allows a display of the ultrasound acquisitions to mirror an examination process of the subject. This allows for review of the manner in which the ultrasound acquisitions were obtained (e.g. by a colleague, review panel or observer). Such an embodiment thereby advantageously provides additional information about the subject, as the timing or pattern of acquiring different ultrasound acquisitions may reflect a suspected diagnosis of the subject.

Optionally, the method may further comprise: receiving a second user input; identifying a location of a region of interest in the 3D ultrasound image based on the second user input; obtaining information about the region of interest; and generating display data for display of the 3D ultrasound image and the information about the region of interest, with the display of the information about the region of interest being based on the location of the region of interest.

Preferably, the information about the region of interest comprises an annotation or measurement for the region of interest. The information may therefore comprise textual information or any other annotations (e.g. a circle or diagram). The second user input may thereby define further information of the 3D ultrasound image. The information of the region of interest may be obtained from the user input, from the additional ultrasound acquisition or from processing of the 3D ultrasound image (e.g. image processing, analysis or recognition).

In some examples, the information about the region of interest is associated with an additional ultrasound acquisition. In this way, a user input may provide information about the additional ultrasound acquisition (e.g. a label or annotation). This enables a user to provide additional information for a subsequent user of the method, e.g. for the purposes of review.

Thus, in some examples, there is proposed a concept of receiving a third user input; and modifying the additional ultrasound acquisition based on the third user input to thereby provide additional information. The modification may be performed prior to generation of the display data for display of the additional ultrasound acquisition. Alternatively, the display data may be modified to reflect the modification to the additional ultrasound acquisition.

Thus, a user may modify an additional ultrasound acquisition, for example, to add labels, measurements or data to the acquisition. This advantageously allows user to add and control the information provided by the additional ultrasound acquisition.

In at least one embodiment, the step of obtaining the additional ultrasound acquisition comprises obtaining a plurality of additional ultrasound acquisitions of respective portions of interest of the volume; the step of identifying a location of the additional ultrasound acquisition comprises identifying, for each additional ultrasound acquisition, a respective location of the additional ultrasound acquisition with respect to the 3D ultrasound image; and the step of generating second display data for display of the 3D ultrasound image and a selection of the additional ultrasound acquisitions by a 3D ultrasound image display, with the display of the selection of additional ultrasound acquisitions being based on the location of each selected additional ultrasound acquisition, wherein the selection of the additional ultrasound acquisitions comprises fewer than the total number of additional ultrasound acquisitions.

Thus, there is proposed a general concept in which two or more additional ultrasound acquisitions are obtained, but the display data is controlled so that not all of the obtained ultrasound acquisitions are displayed at a same time. This significantly reduces a processing power required to display the additional ultrasound images, whilst enabling the additional ultrasound images to be available for display.

Embodiments also provide a computer program product comprising a computer-readable storage medium having computer-readable program code embodied therewith, the computer-readable program code configured to perform all of the steps of any herein described method.

Other embodiments in accordance with examples of the invention provide a three-dimensional, 3D, ultrasound image processing system adapted to obtain a 3D ultrasound image of a volume from an ultrasound imaging system comprising an ultrasound probe and an ultrasound probe tracker; obtain, from the ultrasound imaging system, an additional ultrasound acquisition of a portion of interest of the volume; identify a location of the additional ultrasound acquisition relative to the 3D ultrasound image; and generate display data for display of the 3D ultrasound image and the additional ultrasound acquisition by a 3D ultrasound image display, with the display of the additional ultrasound acquisition being based on the location of the additional ultrasound acquisition.

There may be provided a three-dimensional, 3D, ultrasound image display system comprising a 3D ultrasound image processing system as herein described; and a 3D ultrasound image display adapted to receive the display data; and display the 3D ultrasound image and the additional ultrasound acquisition, with the display of the additional ultrasound acquisition being based on the location of the additional ultrasound acquisition.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a method and processing system for providing a three-dimensional, 3D, ultrasound image along with an additional ultrasound acquisition. A location of the additional ultrasound acquisition with respect to the three-dimensional ultrasound image is determined or obtained. After obtaining the 3D ultrasound image and the additional ultrasound acquisition, initial display data is for display of only the 3D ultrasound image. In response to a user input, second display data is generated for displaying both the 3D ultrasound image and the additional ultrasound acquisition. The display of the additional ultrasound acquisition is based on the location of the additional ultrasound acquisition with respect to the three-dimensional ultrasound image.

Embodiments are at least partly based on the realization that an understanding of a three-dimensional ultrasound image can be enhanced by enabling the provision of additional ultrasound acquisitions. By basing a provision or display of additional ultrasound acquisitions on locations of the acquisitions relative to the three-dimensional ultrasound image, a correlation between the 3D ultrasound image and the acquisitions can be more easily understood. Basing the display on locations of the acquisitions thereby provides an observer of the display with more information than non-location based display of additional ultrasound acquisitions.

Illustrative embodiments may, for example, be employed in medical ultrasound imaging systems, where additional ultrasound acquisitions represent images of different organs, bones, blood vessels, tumors and the like. Preferably, the additional ultrasound acquisitions are functional images or videos, such as Doppler cine loops.

The term 'ultrasound acquisition' describes any data obtainable by an ultrasound probe/system following an ultrasound imaging process. An ultrasound acquisition may be an image, video or cine loop of an area/region of interest imaged by an ultrasound probe.

Figure 1:
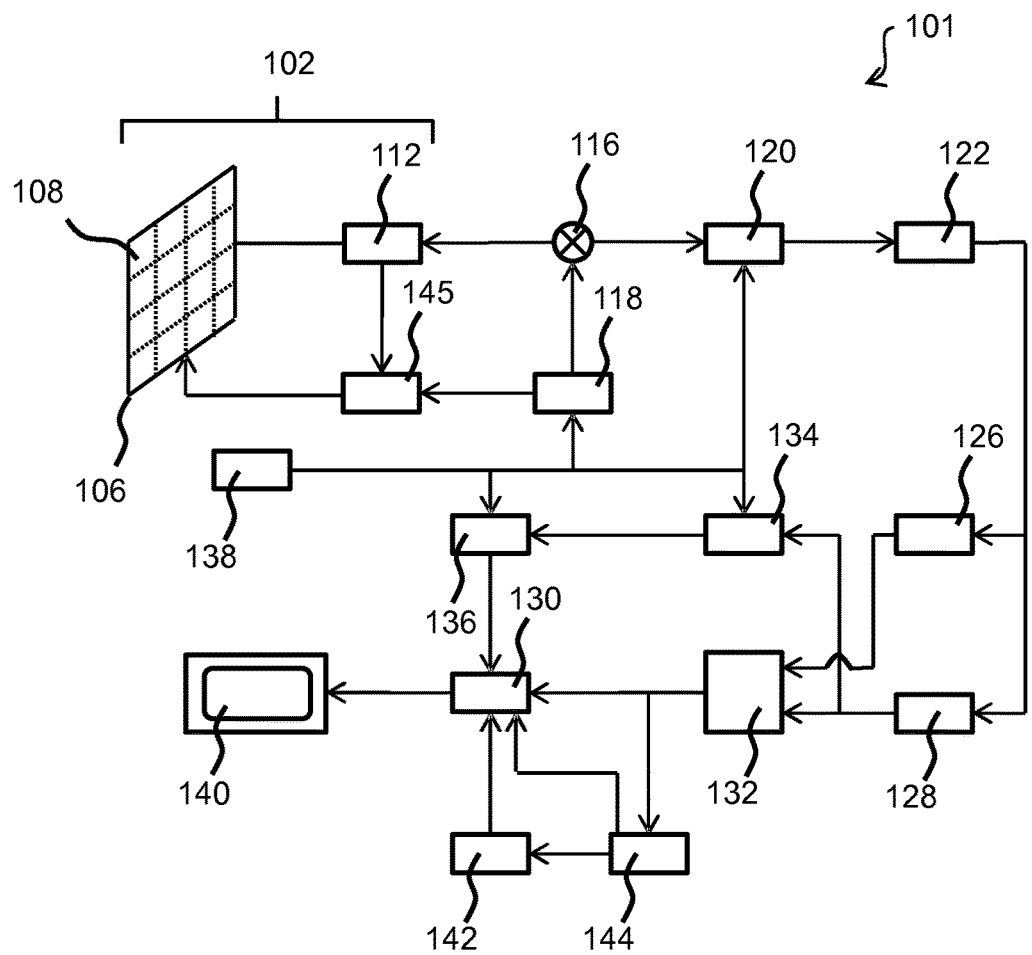
FIG. 1 shows an ultrasound diagnostic imaging system.

An ultrasound imaging system will be hereafter described to help contextualize the present invention. FIG. 1 shows an ultrasound diagnostic imaging system 101 with an array transducer probe 102 in block diagram form.

The array transducer probe 102 comprises transducer cells. Traditionally, piezoelectric materials have been used for ultrasonic transducers. Examples are lead zirconate titanate (PZT) and polyvinylidene difluoride (PVDF), with PZT being particularly popular as the material of choice. The piezoelectric effect is a reversible process, meaning mechanically deformed piezoelectric crystals produce an internal electrical charge as well as a mechanical strain when experiencing an applied electric field. The introduction of an alternating current (AC) to a piezoelectric material creates ultrasound pressure waves at a frequency related to the AC frequency. Single crystal piezoelectric materials can be used to achieve high piezoelectric and electromechanical coupling constants for high-performance transducers. Recent developments have resulted in medical ultrasound transducers that can be batch manufactured by semiconductor processes. Desirably, these processes should be the same ones used to produce the application specific integrated circuits (ASICs) needed by an ultrasound probe, such as a complementary metal-oxide-semiconductor (CMOS) process, particularly for 3D ultrasound. These developments have resulted in micromachined ultrasonic transducers (MUTs), the preferred form being the capacitive MUT (CMUT). CMUT transducers are tiny diaphragm-like devices with electrodes that convert the sound vibration of a received ultrasound signal into a modulated capacitance.

CMUT transducers are able to function over a broad bandwidth, enable high resolution and high sensitivity imaging, and produce a large pressure output so that a large depth of field of acoustic signals can be received at ultrasonic frequencies.

FIG. 1 shows a transducer array 106 of above-described CMUT cells 108 for transmitting ultrasonic waves and receiving echo information. The transducer array 106 of the system 101 may be a one- or a two-dimensional array of transducer elements capable of scanning in a 2D plane or in three dimensions for 3D imaging.

The transducer array 106 is coupled to a micro-beamformer 112 that controls transmission and reception of signals by the CMUT array cells. Beamforming is a method of signal processing that allows directional transmittance, or reception, of a signal such as ultrasound. Signals at particular angles undergo constructive or destructive interference in the transducer array 106 that allows desired signals to be selected and others ignored. Receive beamforming may also utilize a time delay for receiving signals due to the differences in echo depths.

Micro-beamformers are capable of at least partial beamforming by the application of delay-and-sum beamforming of the signals received by adjacent or small groups of transducer elements, e.g. as described in U.S. Pat. No. 5,997,479 (Savord et al.), U.S. Pat. No. 6,013,032 (Savord), and U.S. Pat. No. 6,623,432 (Powers et al.). Micro-beamforming is often carried out inside the probe to reduce the number of signals sent to the main beamformer for processing.

The micro-beamformer 112 is coupled by a probe cable, e.g., coaxial wire, to a transmit/receive (T/R) switch 116 which switches between transmission and reception modes. The T/R switch protects a main beamformer 120 from high energy transmit signals when a micro-beamformer is not present or not used. The transducer array 106 is directly controlled by the main system beamformer 120. The transmission of ultrasonic beams from the transducer array 106 under control of the micro-beamformer 112 is directed by a transducer controller 118 coupled to the micro-beamformer by the T/R switch 116 and the main system beam former 120, which receives input from a user's operation of a user interface or control panel 138. One of the functions controlled by the transducer controller 118 is the direction in which beams are steered and focused. Beams may be steered straight ahead from (orthogonal to) the transducer array 106, or at different angles for a wider field of view possibly by delaying excitation pulses sent from the array transducer cells.

The transducer controller 118 may be coupled to control a voltage source 145 for the transducer array. For instance, the voltage source 145 may define DC and AC bias voltage(s) that are applied to the CMUT cells of a CMUT array 106, e.g., to generate the ultrasonic RF pulses in transmission mode.

The partially beam-formed signals produced by the micro-beamformer 112 are forwarded to the main beamformer 120 where partially beam-formed signals from individual patches of transducer elements are combined into a fully beam-formed signal. For example, the main beamformer 120 may have 128 channels, each of which receives a partially beam-formed signal from a patch of dozens or hundreds of CMUT transducer cells 108. In this way, the signals received by thousands of transducer elements of a transducer array 106 can contribute efficiently to a single beam-formed signal.

The beam-formed signals are coupled to a signal processor 122. The signal processor 122 can process the received echo signals in various ways, such as: bandpass filtering, the passing of frequencies within a given range and the attenuation of frequencies outside that range; decimation, the process of reducing the sampling rate of a signal by some typical order of magnitude or integer value; I and Q component separation, the demodulation of a wave and its sample 80 degrees out of phase; harmonic signal separation, which acts to separate linear and nonlinear signals so as to enable the identification of nonlinear (higher harmonics of the fundamental frequency) echo signals returned from tissue and microbubbles.

The signal processor 122 optionally may perform additional signal enhancement such as: speckle reduction, the removal of interfering waves of the same frequency; signal compounding, a number of ultrasound signals from a given target are combined into a single signal by combining the data received from each angle; or noise elimination, removal of random or systematic noise from a signal.

The bandpass filter in the signal processor 122 may be a tracking filter, with a passband sliding from a higher frequency band to a lower frequency band as echo signals are received from increasing depths, thereby rejecting the noise at higher frequencies from greater depths where these frequencies are devoid of anatomical information. The processed signals are coupled to a Bright-mode (B-mode) processor 126 and optionally to a Doppler processor 128. The B-mode processor 126 employs detection of amplitude of the received ultrasound signal for the imaging of structures in the body, such as the tissue of organs and vessels, and normalizes those amplitudes onto a greyscale to be later displayed as an image. B-mode images of the structure of the body may be formed in harmonic image mode. Harmonic image mode is the exploitation of the non-linear propagation of ultrasound through the body and its tissues. Harmonic imaging transmits at one frequency and receives at the harmonic of this frequency. Typically, the 2nd harmonic is used as higher harmonics have very low amplitude and are hard to detect. B-mode images could be formed in the fundamental image mode or a combination of fundamental and harmonic image modes. The inclusion of harmonic imaging allows for greater contrast and spatial resolution. Previous work has been done on the amalgamation of image modes and algorithms on such combinations are explained further in U.S. Pat. No. 6,283,919 (Roundhill et al.) and U.S. Pat. No. 6,458,083 (Jago et al.).

The Doppler processor 128, if present, processes temporally distinct signals from tissue movement and blood flow for the detection of the motion of substances, such as the flow of blood cells in the image field. The Doppler processor typically includes a wall filter with parameters that may be set to pass and/or reject echoes returned from selected types of materials in the body. For instance, the wall filter can be set to have a passband characteristic, which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field; the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. The structural and motion signals produced by the B-mode (and Doppler) processor(s) are coupled to a scan converter 132 and a multiplanar reformatter 144. The scan converter 132 arranges the echo signals in the spatial relationship from which they were received in the desired image format. For instance, the scan converter may arrange the echo signal into a two dimensional (2D) sector-shaped format, or a pyramidal three-dimensional (3D) image.

The scan converter can overlay a B-mode structural image with colors corresponding to motion at points in the image field with their Doppler-estimated velocities to produce a color Doppler image that depicts the motion of tissue and blood flow in the image field. The multiplanar reformatter 144 will convert echoes that are received from points in a common plane in a volumetric region of the body into an ultrasonic image of that plane, as described further in U.S. Pat. No. 6,443,896 (Detmer). The minimum amount of data points required to describe a plane is 3, one can then move in a direction orthogonal to the plane some fixed amount after measuring those 3 points and repeat that plane measurement, thus building a volumetric region without acquiring data from the entire volume itself. A volume renderer 142 converts the echo signals of a 3D data set into a projected 3D image as viewed from a given reference point as described in U.S. Pat. No. 6,530,885 (Entrekin et al.)

The 2D or 3D images are coupled from the scan converter 132, multiplanar reformatter 144, and volume renderer 142 to an image processor 130 for further enhancement, buffering and temporary storage for display on an image display 140. In addition to being used for imaging, the blood flow values produced by the Doppler processor 128 and tissue structure information produced by the B-mode processor 126 are coupled to a quantification processor 134. The quantification processor produces measures of different flow conditions such as the volume rate of blood flow as well as structural measurements such as the sizes of organs and gestational age, for example. The quantification processor may receive input from the user control panel 138, such as the point in the anatomy of an image where a measurement is to be made.

Output data from the quantification processor is coupled to a graphics processor 136 for the reproduction of measurement graphics and values with the image on the display 140. The graphics processor 136 can also generate graphic overlays for display with the ultrasound images. These graphic overlays can contain standard identifying information such as patient name, date and time of the image, imaging parameters, and the like. For these purposes, the graphics processor receives input from the user interface 138, such as patient name, date of birth etc.

The user interface 138 is also coupled to the transmit controller 118 to control the generation of ultrasound signals from the transducer array 106 and hence the images produced by the transducer array 106 and the ultrasound imaging system 101. The user interface 138 is also coupled to the multiplanar reformatter 144 for selection and control of the planes of multiple multiplanar reformatted (MPR) images that may be used to perform quantified measures in the image field of the MPR images.

As will be understood by the skilled person, the above embodiment of an ultrasound diagnostic imaging system is intended to give a non-limiting example of such an ultrasound diagnostic imaging system. The skilled person will immediately realize that several variations in the architecture of the ultrasound diagnostic imaging system are feasible without departing from the teachings of the present invention. For instance, as also indicated in the above embodiment, the micro-beamformer 112 and/or the Doppler processor 128 may be omitted, the ultrasound probe 102 may not have 3D imaging capabilities and so on. Other variations will be apparent to the skilled person.

Figure 2:
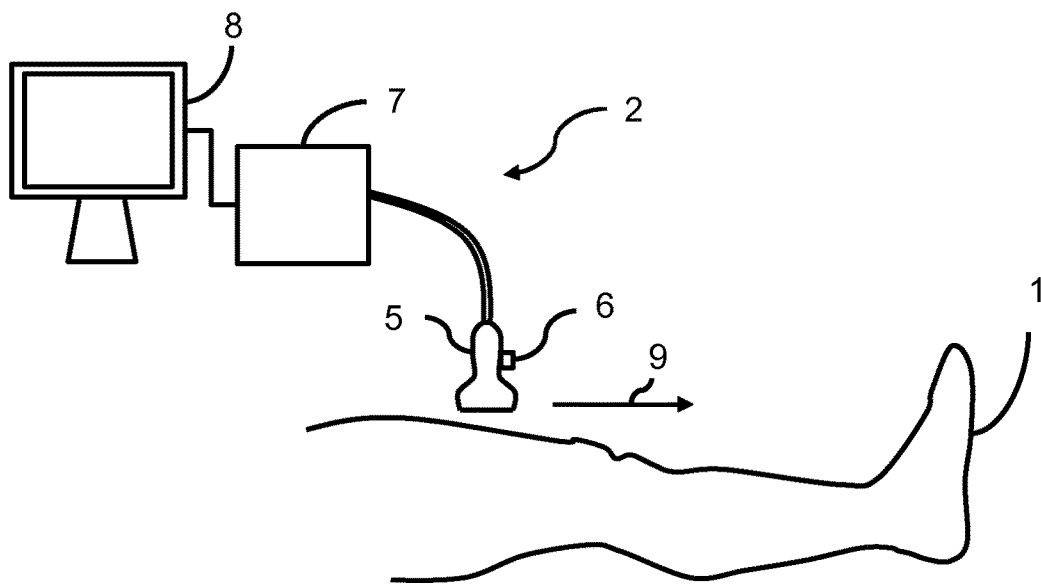
FIG. 2 shows an ultrasound imaging system according to an embodiment.

It will be understood that the present invention is not limited to the described ultrasound diagnostic imaging system, but may rather relate to any ultrasound imaging system. Such ultrasound systems may be adapted to operate in a variety of ultrasound modes, such as: A-mode (Amplitude Modulation), B-mode (Brightness Modulation), M-mode (Motion Mode), Doppler imaging, Harmonics imaging, contrast visualization and so on FIG. 2 illustrates a subject 1 undergoing a three-dimensional, 3D, ultrasound imaging process performed by an ultrasound imaging system 2, such as that previously described. The subject 1 comprises a patient's leg.

The ultrasound imaging system 2 comprises an ultrasound probe 5 and an ultrasound probe tracker 6. The ultrasound probe 5 comprises a handheld portable probe that is manually movable by a user over an area of interest. The ultrasound probe 5 is adapted to capture a two-dimensional image. The ultrasound probe tracker 6 comprises any known ultrasound probe tracker, such as found in an electromagnetic tracked probe.

A three-dimensional, 3D, ultrasound image processing system 7 is adapted to generate display data for display of a 3D ultrasound image by a 3D ultrasound image display 8. In particular, the 3D ultrasound image processing system may obtain signals from the ultrasound imaging system, store the signals and/or process the signals for display of the 3D ultrasound image.

To perform a three-dimensional ultrasound imaging process, the user performs a sweep over the volume of interest (e.g. an upper leg of a subject). In one example, the user brings the ultrasound probe 5 into contact with the subject, initiates an image capturing process and moves the ultrasound probe along a direction of interest 9 as the ultrasound probe captures a series of 2D ultrasound images. The ultrasound probe tracker 6 monitors and records a location of the ultrasound probe when each image is captured. The user ends the image capture process when a volume of interest has passed below the ultrasound probe (e.g. the user has moved the ultrasound probe over the entirety of the subject's upper leg).

The initiation and end of the image capturing process may be performed by a user input, such as a user pressing a button.

The ultrasound image processing system 7 may be able, for example, to reconstruct the 3D volume or ultrasound image from the captured series of 2D ultrasound images. This reconstruction takes into account the relative spatial positioning of each image captured during the sweep. By way of example, a reconstruction process may comprise stacking the captured images based on their relative location, and extrapolating between intermediate volumes (e.g. between each captured images) to generate a 3D ultrasound image.

In normal imaging conditions, e.g. where the subject is stationary throughout the imaging process, the above-described method provides a reconstructed 3D volume or three-dimensional ultrasound image of acceptable quality in all dimensions.

Other methods of generating a 3D volume or reconstructing a 3D ultrasound image based on a series of two-dimensional ultrasound images are known in the art. For example, an ultrasound probe may be adapted to capture a three-dimensional ultrasound image by simultaneously capturing a number of 2D ultrasound images, which is output to the ultrasound image processing system. In other examples, an array of suitably arranged ultrasound probes is used. In some examples, the ultrasound imaging system performs the reconstruction of the 3D ultrasound image.

The 3D ultrasound image display 8 is adapted to obtain display data from the ultrasound image processing system 7 to display the 3D ultrasound image. The three-dimensional ultrasound image can be displayed to a user via, for example, a monitor or screen of the 3D ultrasound image display 8.

The 3D ultrasound image display 8, ultrasound image processing system 7 and ultrasound imaging system 2 may communicate with one another either directly or indirectly using any known system. By way of example, the ultrasound image processing system or ultrasound imaging system may store its output in a database—such as on a server, memory stick, cloud storage system or other storage device—which is accessible by the 3D ultrasound image display or ultrasound image processing system respectively. In other examples, there is a direct communication via a wired or wireless communication channel.

Thus, the ultrasound image processing system 7 is able to generate display data for display of a 3D ultrasound image. The 3D ultrasound image display 8 is adapted to receive the display data and display at least the 3D ultrasound image based on the display data.

The ultrasound image processing system 7 may regenerate or modify the display data, to change the display of the 3D ultrasound image display 8. For example, a user may wish to manipulate an orientation or view of the 3D ultrasound image provided by the display. The display data may therefore be modified in response to a user input to reorient, reposition or relocate the 3D ultrasound image displayed by the 3D ultrasound image display. Such concepts are known in the art.

In the proposed invention, the ultrasound image processing system 7 is adapted to generate second display data for display of the 3D ultrasound image and at least one additional ultrasound acquisition of a portion of interest. In particular, initial or first display data displays the 3D ultrasound image (and not the additional ultrasound acquisition(s)). In response to a user input, second display data is generated for displaying both the 3D ultrasound image and the at least one additional ultrasound acquisition.

An additional ultrasound acquisition may be one captured/acquired by the ultrasound imaging system 2. Capture of the additional ultrasound acquisition may require the ultrasound probe being kept at a selected location on the subject for a minimum length of time. This may not be possible when performing capture of the data for the 3D ultrasound image (e.g. due to memory or time restrictions when capturing the 3D ultrasound image). Moreover, it may not be possible to perform simultaneous capture of the 3D ultrasound image and an additional ultrasound image.

By way of example, the additional ultrasound acquisition may necessitate capture of a series of 2D images of a region of interest at a particular location of the subject. The series of 2D ultrasound images can be processed, according to known concepts, to generate a functional ultrasound video of the region of interest. One such functional ultrasound video or image is the color Doppler image previously described.

In other examples, the additional ultrasound acquisition is a high quality or contrast-enhanced ultrasound image. High quality or contrast-enhanced images typically require keeping the ultrasound probe at the particular location for a minimum length of time.

In yet other examples, the additional ultrasound acquisition is an XML file that defines changes or modifications to the 3D ultrasound image. For example, the XML file may define a location of blood flow within the 3D image, the location of the blood flow being captured by an ultrasound process (e.g. Doppler capture).

Thus, the additional ultrasound acquisition may define features or information (e.g. blood flow, highlighting, color, tumor presence and so on) of the 3D ultrasound image.

The additional ultrasound acquisition thereby provides more or more specific information than available with the 3D ultrasound image alone. In most acquisition settings, where the acquisition provides an image/video, the additional acquisitions are of a higher quality than those captured during the 3D ultrasound imaging process, due to the availability of increased image capture time and non-movement of the ultrasound probe.

In yet other embodiments, a user may define an additional ultrasound acquisition. In such embodiments, the additional ultrasound acquisition may be a segment or extract of the 3D ultrasound image. The location of the additional ultrasound acquisition may be defined by the location of the extract from the 3D ultrasound image. Optionally, the user may be able provide annotation (e.g. texts, graphical shapes or numerical indicators) on the extracted additional ultrasound acquisition. Such embodiments may be useful for marking a location at which further investigation or ultrasound imaging is desired, or for providing additional information (e.g. in the form of annotations) for later use. It will be clear that the additional ultrasound acquisition is still derived from information provided by the ultrasound imaging system 2.

The present invention proposes a concept in which the display of the additional ultrasound acquisition depends upon the location of the additional ultrasound acquisition relative to the 3D ultrasound image. Thus, the second display data generated by the image processing system 7 depends upon the location of the additional ultrasound acquisition.

The location of the additional ultrasound acquisition may be recorded by the ultrasound probe tracker 6, by recording the location at which the additional ultrasound acquisition is captured. This recorded location may be used to establish a relative location of the additional ultrasound acquisition with respect to the 3D ultrasound image.

As the same ultrasound probe tracker 6 is used in the generation of the 3D ultrasound image, the recorded location is correctly calibrated to the 3D ultrasound image. The ultrasound probe tracker 6 may therefore readily define the relative location of the additional ultrasound acquisition with respect to the 3D ultrasound image. Such an embodiment provides the greatest accuracy in determining the relative location of the additional ultrasound acquisition.

In another example, a user may manually define the location of an additional ultrasound acquisition, e.g. using a user input device. By way of example only, a display may display the 3D ultrasound image, and the user may select a location by selecting the appropriate location using a user input device.

In yet other examples, a location of the additional ultrasound acquisition may be identified through image recognition processes or through image comparison processes, which can compare a captured additional ultrasound acquisition to the 3D ultrasound image to identify a location of the additional ultrasound acquisition within the 3D ultrasound image. In particular, a portion of interest within the additional ultrasound acquisition may be identified (e.g. a particular organ) and the location of that portion within the 3D ultrasound image may be identified as the relative location.

The relative location of an additional ultrasound acquisition may, for example, define a display location, a display timing (i.e. when an additional ultrasound image is displayed) or whether the additional ultrasound acquisition is displayed or not. In this way, the relative location (to the 3D ultrasound image) of the additional ultrasound acquisition may define whether the display data contains (display) data of the additional ultrasound acquisition and/or the location of the additional ultrasound acquisition.

The first and second display data is generated after the 3D ultrasound image and additional ultrasound acquisition(s) are obtained.

Particularly advantageous embodiments that use user-selectable markers to identify locations of the ultrasound acquisitions will be described with reference to FIGS. 3 to 4.

In such embodiments, initially generated display data (first display data) defines user-selectable markers for the 3D ultrasound image. Each user-selectable marker is positioned (within the 3D ultrasound image) at a location of a respective additional ultrasound acquisition and is associated with that additional ultrasound acquisition.

In response to a user selecting the user-selectable marker, subsequent display data (second display data) is generated for display of both the 3D ultrasound image and the additional ultrasound acquisition associated with the marker. In this way, the additional ultrasound acquisition is not displayed (e.g. by an ultrasound image display) until its associated marker is selected.

Put another way, initial display data (first display data) contains data for display of the 3D ultrasound image and information about the location of additional ultrasound acquisitions. In response to receiving a user input, the initial display data is modified (i.e. to create second display data) to further comprise data for display of an additional ultrasound acquisition associated with the user input, e.g. selection of an appropriate marker.

Providing a user-selectable marker permits a user to search and retrieve stored ultrasound acquisitions more efficiently. In particular, displaying an ultrasound acquisition only in response to a selection of a corresponding marker provides a user with a simultaneous overview of the presence and availability of various ultrasound acquisitions, and increases a user's cognizance of the total amount of information available. There is also a reduction in an amount of memory and processing power, including number of memory accesses, required to provide a user with relevant ultrasound acquisitions, as an ultrasound acquisition need only be retrieved (e.g. from a database) when a corresponding marker is selected by a user.

Moreover, in the context of a clinical analysis of a 3D ultrasound image, provision of a marker at the location of a portion of interest reduces a likelihood of clinician error, and reduces the risk of a clinician misunderstanding, misidentifying or incorrectly locating the portion of interest, which could increase subject risk. By way of example, if a location of a tumor is misidentified by a clinician, this could lead to unnecessary or harmful treatment of the subject at an incorrect location.

Figure 3:
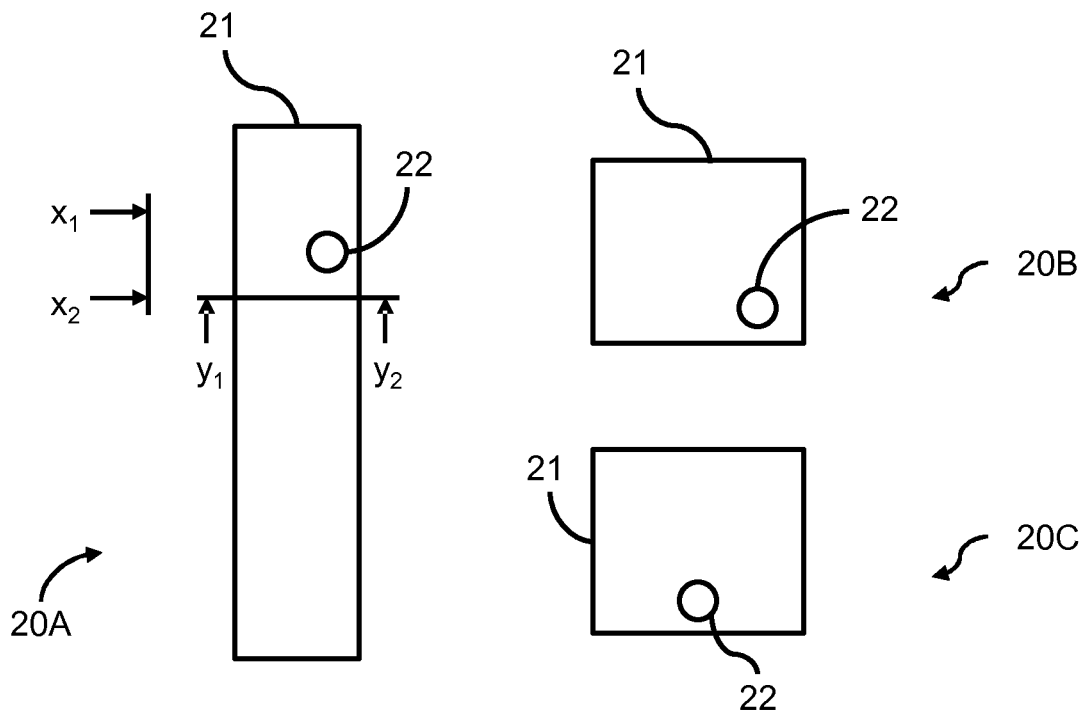
FIGS. 3 and 4 illustrate a display of a three-dimensional ultrasound image according to an embodiment.

FIG. 3 conceptually illustrates a three-dimensional (3D) ultrasound image display 21 of a three-dimensional ultrasound image. The display 21 is generated from the display data (first display data), and may be displayed by the 3D ultrasound image display 8.

Three views of an imaged 3D volume are illustrated for the sake of clarity: a top-down view 20A; an elevation view 20B (viewed from the line $y_1$-$y_2$); and a side view 20C (viewed from the line $x_1$-$x_2$).

As previously explained, the display data contains data for display of the 3D ultrasound image. The display data is processed by the 3D ultrasound image display 8 to thereby display the 3D ultrasound image display 21.

The display data also defines a location of an additional ultrasound acquisition. The 3D ultrasound image display 21 thereby identifies a location of an additional ultrasound acquisition (a "location of interest"). The location of interest is defined relative to the imaged 3D volume or the 3D ultrasound image.

The defined location of the additional ultrasound acquisition defines a location of a user-selectable marker 22 for display within the displayed 3D ultrasound image. The display 21 of the 3D ultrasound image thereby also displays a user-selectable marker at the identified location of the additional ultrasound acquisition.

Thus, initial or first display data is provided for display of the 3D ultrasound image and for display of one or more user-selectable markers, each respectively associated with an additional ultrasound acquisition.

This initial or first display data (and thereby display 21) is modified in response to a user selecting a user-selectable marker. In particular, the modified display data contains data for display of the 3D ultrasound image and the additional ultrasound acquisition (associated with the selected user-selectable marker 22). Thus, the display 21, in response to a user selecting the user-selectable marker 22, displays the appropriate additional ultrasound acquisition.

Thus, the user-selectable marker 22 is provided at a location of an additional ultrasound acquisition and is mapped or associated with that additional ultrasound acquisition. In response to a user selecting the user-selectable marker, the 3D ultrasound image display displays this additional ultrasound acquisition to the user. The user is able to select the user-selectable marker using any known user input device, such as a touchscreen interface, computer mouse, keyboard and so on.

Figure 4:
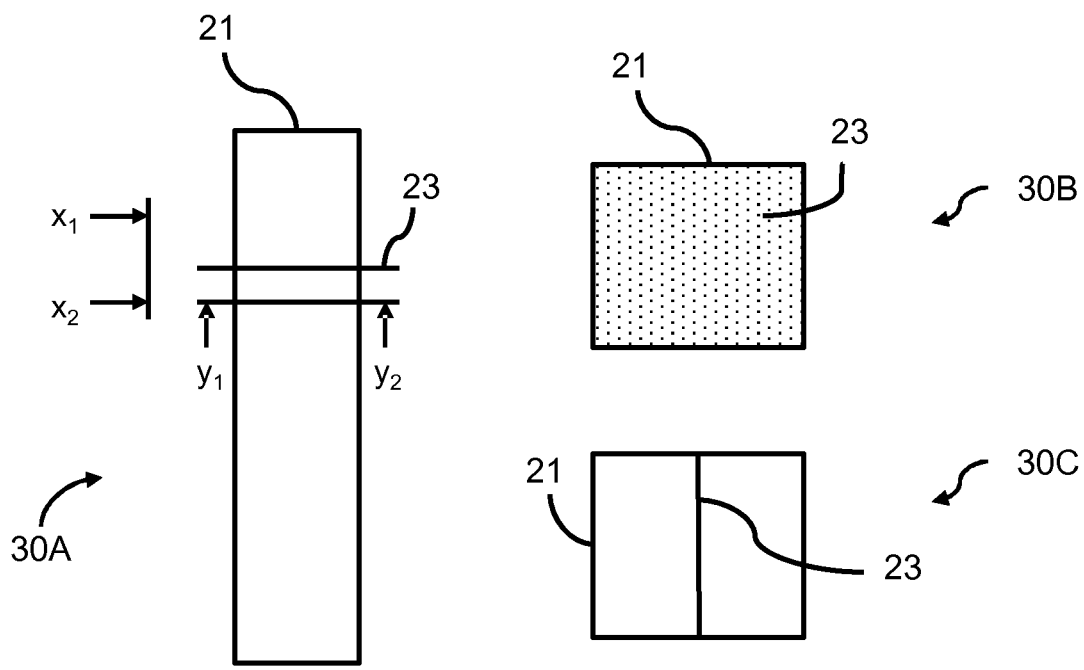

FIG. 4 conceptually illustrates a display of a three-dimensional ultrasound image 21 after a user has selected the user-selectable marker 22. As before, the display 21 is provided from the (modified) display data (second display data), and may be displayed by the 3D ultrasound image display 8.

FIG. 4 illustrates the same three views of the imaged 3D volume 21: a top-down view 30A; an elevation view 30B and a side view 30C. As previously noted, upon selecting the user-selectable marker, the initial or first display data is modified for display of the 3D ultrasound image and the additional ultrasound acquisition. Thus, second display data is provided, the second display data being provided for display of the 3D ultrasound image 21 and the additional ultrasound acquisition 23.

In FIG. 4, the additional ultrasound acquisition comprises a two-dimensional, 2D, ultrasound image or video of the portion of interest.

By only generating display data for display of the 3D ultrasound image 21 and the additional ultrasound acquisition 23 in response to the user-selectable marker 22 being selected by a user, a total amount of data transferred or transmitted for display is reduced (as data of the additional ultrasound acquisition is only transferred when a user-selectable marker is selected). The larger the size of the additional ultrasound acquisition or the greater the number of user-selectable markers, the greater the effect of reducing the total amount of data.

Moreover, providing the user-selectable marker at the location of the portion of interest allows a user to perform a task of diagnosing a problem more efficiently, as the user is made more immediately aware of a location of further information. Thus, the arrangement and location of the user-selectable marker provides cognitive content to a user that was not previously available (indicating a location of the additional ultrasound acquisition).

As illustrated, the display data may be adapted so that the location of the displayed additional ultrasound acquisition 23 also depends upon the location of the user-selectable marker 22. This helps improves a user's understanding of the available information and reduces screen clutter. By way of example, the information may be displayed alongside or at a location indicated by the user-selectable marker.

Thus, the user-selectable marker marking an additional ultrasound acquisition may be replaced by the additional ultrasound acquisition itself, in response to a user selecting that user-selectable marker. In particular, if the additional ultrasound acquisition is a 2D image or video of a portion of interest of the subject, the 2D image/video may overlay (as illustrated in FIG. 4) the appropriate portion of interest of the 3D ultrasound image represented by the additional ultrasound acquisition. Thus, the displayed additional ultrasound acquisition may replace a portion of the 3D ultrasound image.

In other examples, the displayed additional ultrasound acquisition is positioned to a side of the 3D ultrasound image, e.g. in line with the user-selectable marker or with a pointer to the user-selectable marker. The display location of the additional ultrasound acquisition may thereby depend upon the location of the additional ultrasound acquisition relative to the 3D ultrasound image.

In embodiments, the ultrasound image processing system is adapted to obtain a depth of the portion of interest within the additional ultrasound acquisition. As previously explained, the additional ultrasound acquisition may represent an image/video containing a portion of interest (e.g. an organ, bone, tumor, blood vessel and so on).

The depth of the portion of interest may be obtained from a user input device or determined from the information about the portion of interest. In one example, the length of a button press (of a user input device) may indicate a depth of the portion of interest. For example, when capturing an additional ultrasound acquisition using the ultrasound probe, a length of a button press (to capture the location) may indicate a relative depth of the portion of interest. The longer the press, the further the portion of interest from the ultrasound probe.

The (first) display data may be configured so that the displayed user-selectable marker 22 comprises an indication of the depth of the portion of interest with respect to a current view of the 3D ultrasound image. Thus, the user-selectable marker may indicate a position of a portion of interest (associated with an additional ultrasound acquisition) within the overall 3D ultrasound image.

The 3D ultrasound image display may therefore indicate a depth of the portion of interest (to which the additional ultrasound acquisition relates) relative to a current view of the 3D ultrasound image display. The indication may be textual or graphical (e.g. different colors or sizes).

In particular, where the acquisition is an image or video, the depth may represent a distance from an edge of the ultrasound image or a location within the acquisition.

By way of example, a 2D ultrasound image may be an image of a particular organ (the portion of interest), where the organ is located in only a portion of the overall 2D ultrasound image. An image recognition process or user input may identify the location of the organ within the 2D ultrasound image, to establish the position of the organ relative to the edges of the ultrasound image. If the orientation and location of the 2D ultrasound image with respect to the imaged 3D volume is known, the 3D location (i.e. depth) of the organ can be readily identified.

If the position and/or orientation of the 2D image/video with respect to the 3D imaged volume is known, the depth of the portion of interest (within that image/video) with respect to a view of the 3D ultrasound image is readily identifiable. Providing information on the depth increases a user's cognizance of information, beyond that previously available to them.

Whilst FIGS. 3 and 4 only illustrate a single additional ultrasound acquisition and its user-selectable marker, it will be apparent that the ultrasound image processing system may be adapted to obtain a plurality of additional ultrasound acquisitions and provide display data for display of a 3D ultrasound image and a user-selectable marker for each additional ultrasound acquisition.

Figure 5:
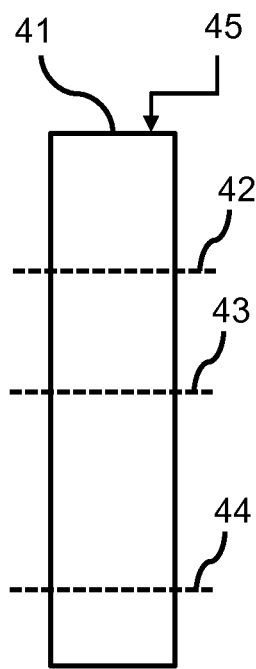
FIG. 5 illustrates a display of a three-dimensional ultrasound image according to another embodiment.

FIG. 5 illustrates another three-dimensional (3D) ultrasound image display 41 of a three-dimensional ultrasound image according to another embodiment. The display 41 is provided based on display data generated by the ultrasound image processing system 7, and may be displayed by the 3D ultrasound image display 8.

Initial (first) display data contains data for display 41 of the 3D ultrasound image, and is provided by the ultrasound image processing system.

The ultrasound image processing system is adapted to obtain a plurality of additional ultrasound acquisitions and identify a location of each ultrasound acquisition relative to the 3D ultrasound image. Here, the plurality comprises a first 42, second, 43 and third 44 additional ultrasound acquisition.

FIG. 5 also illustrates exemplary locations of the first 42, second 43 and third 44 additional ultrasound acquisition relative to the 3D ultrasound image, for the purposes of conceptual understanding.

The initial display data (for display of the 3D ultrasound image only) may be sequentially modified, in response to a first user input, such that the display 41 continually displays the 3D ultrasound image and sequentially displays the plurality of additional ultrasound acquisitions.

In one embodiment, the display data is sequentially modified based on the location of each additional ultrasound acquisition. By way of example, the display data may be sequentially modified so that the display 41 sequentially displays the additional ultrasound acquisitions 42, 43, 44 as they are positioned with respect to a direction.

In one such example, the initial display data may be firstly modified to generate second display data in which the additional ultrasound acquisition 42 associated with a location closest to a predetermined location 45 on the 3D ultrasound image is displayed. The second display data may then be sequentially modified so that increasingly distant additional ultrasound acquisitions 43, 44 are sequentially displayed. Thus, the more distant the location of the additional ultrasound acquisition from the predetermined location, the later in the sequence that said additional ultrasound acquisition is provided the display data. This may, for example, allow for sequential display of additional ultrasound acquisitions from a top of the display (e.g. a top of a user's leg) to a bottom of the display (e.g. a bottom of the user's leg).

In another embodiment, the display data is sequentially modified based on the time at which each additional ultrasound acquisition is obtained or captured.

By way of example, the display data may be sequentially modified so that the oldest (i.e. earliest captured) additional ultrasound acquisition is displayed first, with subsequently captured additional ultrasound acquisitions being displayed in the order of their capture. Thus, the initial display data may be firstly modified so that additional ultrasound acquisition that was captured first is displayed, and then subsequently modified so that the additional ultrasound acquisition which was captured second is displayed, and so on. In this way, the later that an additional ultrasound acquisition was captured, the later in the sequence that additional ultrasound sequence is in the display data.

The sequential modification to the initial display data, to generate the second display data, is triggered by a user input. By way of example, a user may define a location of a predetermined location 45 (or desired direction) on the displayed 3D ultrasound image, which triggers a sequential modification to the initial display data based on distance from the predetermined location 45.

In another example, a user may define a start time for display of additional ultrasound acquisitions, and the display data is modified so that a sequence of additional acquisitions captured after that start time is sequentially included (from earliest to latest) in the display data.

The display data is modified so that the relevant additional ultrasound acquisition(s) is displayed at the location of the additional ultrasound acquisition on the displayed 3D ultrasound image. This provides a user with additional information and prevents confusion or misinterpretation.

Thus, the display data may be sequentially modified so that a plurality of additional ultrasound acquisitions are sequentially displayed in either an order of acquisition or an order as determined during post-processing of the additional ultrasound acquisitions. Thus, post-processing of the additional ultrasound acquisitions may be performed to determine a sequence order (e.g. along a particular direction).

Thus, embodiments propose to sequentially modify the display data to provide a sequential display of additional ultrasound acquisitions. The order of the sequential display may be based on, for example, a capture order, a location order, an order representing a typical or known medical examination procedure and so on. Sequential display of the ultrasound acquisitions advantageously reduces an amount of memory required to display the images and also provides additional information to a user or observer (i.e. the order of display provides new information, such as a capture order, beyond that previously available).

Figure 6:
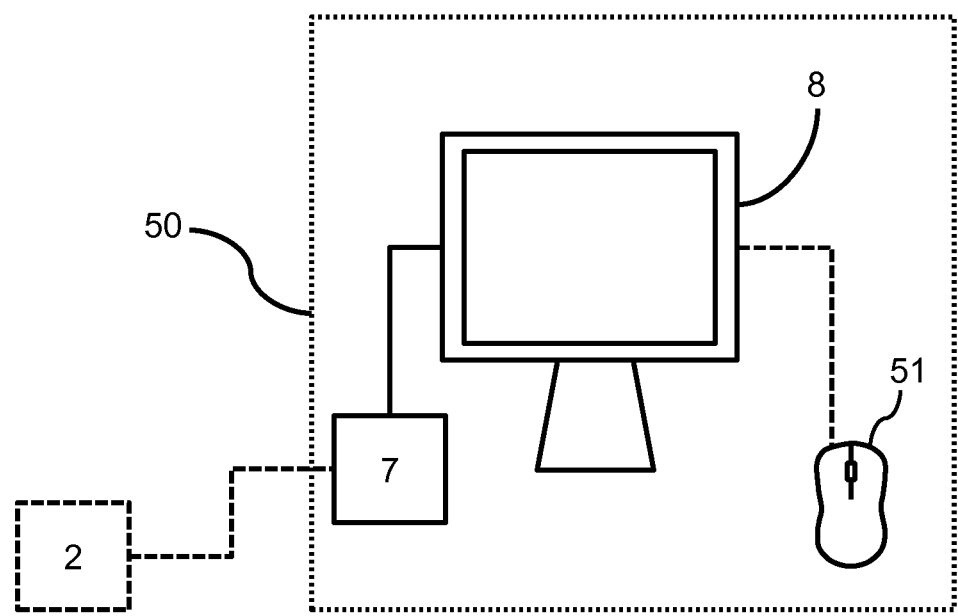
FIG. 6 illustrates a three-dimensional ultrasound image display system according to an embodiment.

FIG. 6 illustrates an ultrasound image display system 50 according to an embodiment of the invention. The ultrasound image display system 50 comprises a three-dimensional ultrasound image processing system 7 and a 3D ultrasound image display 8. The ultrasound image display system 50 also comprises a user input device 51.

The 3D image processing system 7 is adapted to obtain a 3D ultrasound image of a volume from an ultrasound imaging system 2 comprising an ultrasound probe (not shown) and an ultrasound probe tracker (not shown).

The 3D image processing system 7 is also adapted to obtain an additional ultrasound acquisition, of a portion of interest of the volume, and identify a location of the additional ultrasound acquisition within the 3D ultrasound image.

The 3D image processing system 7 obtains signals, directly or indirectly, from the additional ultrasound acquisition from the ultrasound imaging system 2 (e.g. a 2D ultrasound image). The 3D image processing system 7 may identify the location of the additional ultrasound acquisition by obtaining a location from the ultrasound imaging system, e.g. where the ultrasound probe marks a location of the portion of interest or the additional ultrasound acquisition, or the user input device 43.

The 3D image processing system 7 is adapted to provide or generate display data for display of the 3D ultrasound image and the additional ultrasound acquisition, using methods previously described.

The 3D ultrasound image display 8 is adapted to display the 3D ultrasound image. In particular, the 3D ultrasound image display is adapted to receive the display data generated by the 3D image processing system 7. For example, where the display data is the second display data, the 3D ultrasound image display 8 would display the 3D ultrasound image and the additional ultrasound acquisition, with the display of the additional ultrasound acquisition being based on the location of the additional ultrasound acquisition.

Where first display data is for display of the 3D ultrasound image and a user-selectable marker, the user input device 51 allows a user to select the user-selectable marker displayed by the 3D ultrasound image display 8. The user input device may comprise, for example, a mouse, keyboard and/or touch-sensitive interface (e.g. coupled to the display 8).

In some embodiments, the 3D image processing system 7 is adapted to generate the 3D ultrasound image itself. By way of example, the ultrasound imaging system may output a series of 2D ultrasound images, to which the 3D image processing system 7 applies a 3D reconstruction process previously described. In other embodiments, the ultrasound image system 2 provides a reconstructed or captured 3D ultrasound image.

In any of the herein described embodiments, a relative orientation of the additional ultrasound acquisition with respect to the 3D ultrasound image may be obtained. The display data may be adapted so that the orientation of the displayed additional ultrasound acquisition (or an associated user-selectable marker) is based on its relative orientation. In particular, the orientation of the displayed additional ultrasound acquisition may correspond with the orientation of the additional ultrasound acquisition (when captured) relative to the 3D ultrasound image.

Optionally, as the 3D ultrasound image is rotated (e.g. in the display), so the additional ultrasound acquisition is rotated to maintain its relative orientation.

The ultrasound imaging system may capture one or more orientation reference points of the 3D ultrasound image during the 3D ultrasound imaging process. For example, a first orientation reference point may be captured at a beginning of the ultrasound imaging process.

The relative orientation for the displayed information may then be captured by the ultrasound imaging system. For example, the ultrasound probe tracker may determine a relative orientation of the ultrasound probe to the one or more orientation reference points when capturing a location of the portion of interest. The ultrasound probe tracker may comprise a probe orientation determiner for capturing an orientation reference point. The determiner may comprise, for example, an accelerometer, gyrometer or other orientation-determining device.

In this way, both a translational position (i.e. location) and a rotational position (i.e. orientation) of the portion of interest can be used to position the additional ultrasound acquisition or the user-selectable marker.

In some herein described embodiments, information about a portion of interest may be provided by a user. This information may be associated with the 3D ultrasound image or an additional ultrasound acquisition. The information about the portion of interest may comprises mark-up, graphical, textual or numerical information of the portion of interest. By way of example, the information may comprise a measurement of a portion of interest, an annotation of the portion of interest, graphical information associated with the portion of interest, a label for the portion of interest, a highlight of the portion of interest, a graphical overlay for the portion of interest and so on.

In some preferred embodiments, the additional ultrasound acquisition may be modifiable by a user to contain annotations, measurements or other textual/numerical information of a portion of interest. Thus, multiple pieces of information about a portion of interest can be combined into a single additional ultrasound acquisition, reducing a number of memory accesses to provide the information about the portion of interest and increasing an efficiency of the system. The textual/numerical information may be input via the user input 51, which may comprise, for example, a mouse and keyboard combination or a touchscreen.

Textual information may be added to an additional ultrasound acquisition during a capture process of the additional ultrasound acquisition. Thus, a clinician/user may label or indicate other important features during a capture of additional ultrasound acquisition.

Figure 7:
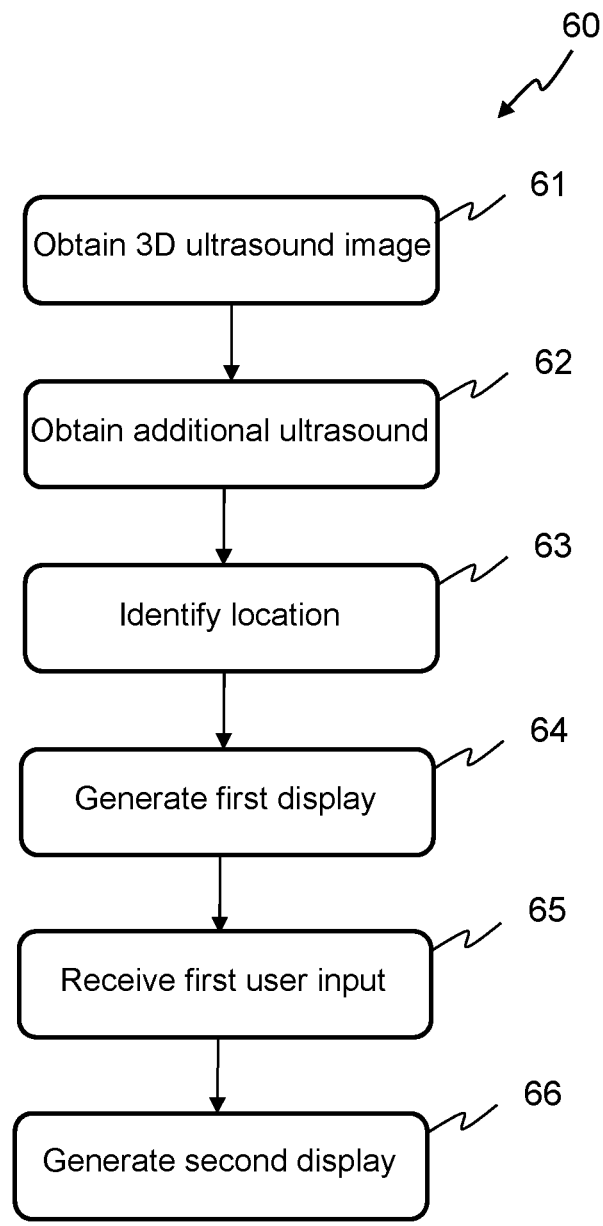
FIG. 7 illustrates a method of providing a three-dimensional, 3D, ultrasound image according to an embodiment.

FIG. 7 illustrates a method 60 of providing a three-dimensional, 3D, ultrasound image with an additional ultrasound acquisition.

The method 60 comprises a step 61 of obtaining a 3D ultrasound image of a volume from an ultrasound imaging system comprising an ultrasound probe and an ultrasound probe tracker.

The method 60 also comprises a step 62 of obtaining, from the ultrasound imaging system, an additional ultrasound acquisition of a portion of interest of the volume.

The method 60 also comprises a step 63 of identifying a location of the additional ultrasound acquisition relative to the 3D ultrasound image.

The method 60 comprises a step 64 of generating first display data for display of the 3D ultrasound image The method 60 also comprises a step 65 of receiving a first user input.

The method also comprises a step 66 of, in response to the first user input, generating second display data for display of the 3D ultrasound image and the additional ultrasound acquisition, with the display of the additional ultrasound acquisition being based on the location of the additional ultrasound acquisition. Thus, step 65 may be a determination step to determine whether a first user input has been received.

Steps 64 to 66 are performed after at least steps 61 and 62 of obtaining the 3D ultrasound image and the additional ultrasound acquisition.

The method may be adapted to carry out any number of steps performed by the three-dimensional ultrasound image processing system previously described.

In all described embodiments, to avoid over-burdening a memory or processor for the 3D ultrasound image display, there may be a maximum number of displayed additional ultrasound acquisitions. Thus, the display data may be adapted to only provide for display of a limited number of additional ultrasound acquisitions. By way of example, if more than a predetermined number (e.g. 5) of additional ultrasound acquisition is expected, the display data associated with the longest display time (e.g. that additional ultrasound acquisition which has been displayed for the longest) may be removed from display.

In all described embodiments, the method or image processing system may be adapted so that the display data removes display data associated with a particular additional ultrasound acquisition in response to a particular user input. By way of example only, inclusion in display data of another additional ultrasound acquisition may remove an earlier additional ultrasound acquisition from the display data. In another example, there may be a user-selectable button for removing data for display of an additional ultrasound acquisition from the display data.

In at least one embodiment, the 3D ultrasound image is displayed so that it is aligned with the main directions of the patient to thereby mimic a conventional CT or MR scan. The ultrasound probe may be adapted to record an orientation in space of the patient (e.g. to identify an axial view of a patient). This may be performed, for example, by placing the probe in alignment with the subject or patient. By way of example, if the subject is a patient on a hospital bed, the probe may be aligned with the main direction of the bed (i.e. arranged to lie in a direction from a head of the bed to a foot of the bed). It is a fair assumption that the patient will be well aligned with the bed, so that the probe can thereby be aligned with the axial direction of a patient. This provides a simple and intuitive mechanism for determining a direction of a patient using an ultrasound probe.

As described in the preceding passages, the additional ultrasound acquisition may be a 2D ultrasound image/video, such as a Doppler or contrast enhanced ultrasound image. Preferably, the 2D ultrasound image/video is of a higher resolution, contrast, quality or informative value than the 3D ultrasound image, or provides information (e.g. blood-flow information) not available in the 3D ultrasound image alone. In this way, provision of a 2D image may significantly increase a clinician's or user's understanding of the imaged volume.

The proposed methods and processing systems are particularly suited to providing additional ultrasound acquisitions in response to a user selecting a user-selectable marker on a display of a 3D ultrasound image, as additional ultrasound acquisitions may require significant processing power and/or memory requirements to retrieve and display. By only displaying additional ultrasound acquisitions when a corresponding marker is selected, an efficiency of the system may be significantly improved without affecting an availability of an image to a clinician or user.

As discussed above, embodiments make use of a three-dimensional ultrasound image processing system. The processing system can be implemented in numerous ways, with software and/or hardware, to perform the various functions required. For example, the processing system may comprise a controller, which employs one or more microprocessors that may be programmed using software (e.g., microcode) to perform the required functions. A processing system may however be alternatively implemented without employing a processor, and also may be implemented as a combination of dedicated hardware to perform some functions and a processor (e.g., one or more programmed microprocessors and associated circuitry) to perform other functions.

Examples of processing system components that may be employed in various embodiments of the present disclosure include, but are not limited to, conventional microprocessors, application specific integrated circuits (ASICs), and field-programmable gate arrays (FPGAs).

In various implementations, a processing system may be associated with one or more storage media such as volatile and non-volatile computer memory such as random access memory (RAM), programmable read-only memory (PROM), electrically programmable read-only memory (EPROM), and electrically erasable and programmable read only memory (EEPROM). The storage media may be encoded with one or more programs that, when executed on one or more processors and/or controllers, perform the required functions. Various storage media may be fixed within a processor or controller or may be transportable, such that the one or more programs stored thereon can be loaded into a processing system.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method of providing a three-dimensional (3D) ultrasound image along with an additional ultrasound acquisition, the method comprising:
    obtaining a 3D ultrasound image of a volume captured by an ultrasound imaging system comprising an ultrasound probe and an ultrasound probe tracker;
    obtaining an additional ultrasound acquisition of a portion of interest of the volume captured by the ultrasound imaging system, and storing the additional ultrasound acquisition, wherein when capturing the additional ultrasound acquisition using the ultrasound probe, a time duration of a button press to capture an identified location of the additional ultrasound acquisition indicates a relative depth of the portion of interest;
    identifying a location of the additional ultrasound acquisition relative to the 3D ultrasound image; and
    after obtaining the 3D ultrasound image and obtaining the additional ultrasound acquisition:
        generating first display data for display of the 3D ultrasound image;
        receiving a first user input requesting display of the additional ultrasound acquisition; and
        in response to the first user input, retrieving the stored additional ultrasound acquisition and generating second display data for replacing a portion of the 3D ultrasound image of the first display data with the additional ultrasound acquisition at the location of the additional ultrasound acquisition; and
    displaying the 3D ultrasound image with the additional ultrasound acquisition overlaying the 3D ultrasound image at the location of the additional ultrasound acquisition based on the second display data.

2. The method of claim 1, wherein:
    the first display data is for display of the 3D ultrasound image and a user-selectable marker, a display location of the user-selectable marker being based on the location of the additional ultrasound acquisition; and receiving the first user input comprises receiving a first user input in response to a user selecting the user-selectable marker.

3. The method of claim 1, further comprising determining an orientation of the additional ultrasound acquisition with respect to the 3D ultrasound image, wherein displaying the additional ultrasound acquisition is based on the determined orientation of the additional ultrasound acquisition.

4. The method of claim 1, wherein identifying the location of the additional ultrasound acquisition comprises obtaining the location from the ultrasound probe tracker.

5. The method of claim 1, further comprising:
obtaining a plurality of additional ultrasound acquisitions of different portions of interest of the volume captured by the ultrasound imaging system; and
identifying respective additional locations of the plurality of additional ultrasound acquisitions relative to the 3D ultrasound image,
wherein generating the second display data further comprises replacing other portions of the 3D ultrasound image of the first display data with the plurality of additional ultrasound acquisitions at the respective additional locations of the plurality additional ultrasound acquisitions; and
displaying the 3D ultrasound image with the plurality of additional ultrasound acquisitions overlaying the 3D ultrasound image at the respective additional locations based on the second display data.

6. The method of claim 5, wherein displaying the 3D ultrasound image with the plurality of additional ultrasound acquisitions overlaying the 3D ultrasound image comprises:
sequentially displaying each of the plurality additional ultrasound acquisition, with the sequential display of each of the plurality additional ultrasound acquisition being based on the respective additional locations of each of the plurality of additional ultrasound acquisitions.

7. The method of claim 5, wherein displaying the 3D ultrasound image with the plurality of additional of the plurality ultrasound acquisitions overlaying the 3D ultrasound image comprises:
sequentially displaying each of the plurality additional ultrasound acquisition, with the sequential display of each of the plurality additional ultrasound acquisition being based on a respective time at which each of the plurality additional ultrasound acquisition was captured by the ultrasound imaging system.

8. The method of claim 1, further comprising:
receiving a second user input;
identifying a location of a region of interest in the 3D ultrasound image based on the second user input;
obtaining information about the region of interest; and
generating display data for display of the 3D ultrasound image and the information about the region of interest, with the display of the information about the region of interest being based on the location of the region of interest.

9. The method of claim 1, further comprising:
receiving a third user input; and
modifying the additional ultrasound acquisition based on the third user input.

10. The method of claim 1, wherein:
obtaining the additional ultrasound acquisition comprises obtaining a plurality of additional ultrasound acquisitions of respective portions of interest of the volume;
identifying a location of the additional ultrasound acquisition comprises identifying, for each of the plurality additional ultrasound acquisition, a respective location of the additional ultrasound acquisition with respect to the 3D ultrasound image; and
generating the second display data comprises generating display data for replacing at least one other portion of the 3D ultrasound image with a selection of at least one other additional ultrasound acquisition of the plurality of additional ultrasound acquisitions by a 3D ultrasound image display, with a display of the selection of the at least one other additional ultrasound acquisition being based on the location of the selected at least one other additional ultrasound acquisition,
wherein the selection of the at least one other additional ultrasound acquisition comprises fewer than a total number of the plurality of additional ultrasound acquisitions.

11. A three-dimensional (3D) ultrasound image processing system comprising:
an ultrasound probe configured to capture ultrasound images;
an ultrasound probe tracker configured to monitor and record locations of the ultrasound probe capturing the ultrasound images;
an ultrasound image display; and
an ultrasound image processing system configured to:
capture a 3D ultrasound image of a volume from using the ultrasound probe;
capture an additional ultrasound acquisition of a portion of interest of the volume using the ultrasound probe, wherein when capturing the additional ultrasound acquisition using the ultrasound probe, a time duration of a button press to capture an identified location of the additional ultrasound acquisition indicates a relative depth of the portion of interest;
store the additional ultrasound acquisition; and
after obtaining the 3D ultrasound image and obtaining the additional ultrasound acquisition,
generate first display data for display of the 3D ultrasound image;
receive a first user input requesting display of the additional ultrasound acquisition;
in response to the first user input, retrieve the stored additional ultrasound acquisition and generate second display data for replacing a portion of the 3D ultrasound image of the first display data with the additional ultrasound acquisition at an identified location of the additional ultrasound acquisition; and
display on the ultrasound image display the 3D ultrasound image with the additional ultrasound acquisition overlaying the 3D ultrasound image at the identified location of the additional ultrasound acquisition based on the second display data.

12. The system of claim 11, wherein the first display data is for display of the 3D ultrasound image and a user-selectable marker, a display location of the user-selectable marker being based on the identified location of the additional ultrasound acquisition.

13. The system of claim 12, wherein the first user input is received in response to selection of the user-selectable marker.

14. The system of claim 11, where the ultrasound image processing system is further configured to determine an orientation of the additional ultrasound acquisition with respect to the 3D ultrasound image, and wherein the ultrasound image display is configured to displaying the additional ultrasound acquisition further based on the determined orientation of the additional ultrasound acquisition.

15. The system of claim 11, wherein ultrasound probe tracker provides the identified location of the additional ultrasound acquisition.

16. The system of claim 11, where the ultrasound image processing system is further configured to:
receive a second user input;
identify a location of a region of interest in the 3D ultrasound image based on the second user input;
obtain information about the region of interest; and
generate display data for display of the 3D ultrasound image and the information about the region of interest on the ultrasound image display, with the display of the information about the region of interest being based on the identified location of the region of interest.

17. A non-transitory computer readable medium storing instructions for providing a three-dimensional (3D) ultrasound image along with an additional ultrasound acquisition that, when executed by a processing system, cause the processing system to:
receive a 3D ultrasound image of a volume, the 3D ultrasound image having been captured by an ultrasound imaging system comprising an ultrasound probe and an ultrasound probe tracker; and
after receiving the 3D ultrasound image:
generate first display data for display of the 3D ultrasound image;
receive a first user input identifying a location in the 3D ultrasound image of an additional ultrasound acquisition of a portion of interest of the volume, the additional ultrasound acquisition having been previously captured and stored by the ultrasound imaging system, wherein when capturing the additional ultrasound acquisition using the ultrasound probe, a time duration of a button press to capture an identified location of the additional ultrasound acquisition indicates a relative depth of the portion of interest;
in response to the first user input, retrieve the stored additional ultrasound acquisition and generate second display data for replacing a portion of the 3D ultrasound image of the first display data with the additional ultrasound acquisition at the location of the additional ultrasound acquisition; and
cause the 3D ultrasound image with the additional ultrasound acquisition overlaying the 3D ultrasound image at the location of the additional ultrasound acquisition to be displayed based on the second display data.

18. A three-dimensional (3D) ultrasound image processing system comprising:
an ultrasound probe configured to capture ultrasound images;
an ultrasound probe tracker configured to monitor and record locations of the ultrasound probe capturing the ultrasound images;
an ultrasound image display; and
an ultrasound image processing system configured to:
capture a 3D ultrasound image of a volume from using the ultrasound probe;
capture an additional ultrasound acquisition of a portion of interest of the volume using the ultrasound probe, wherein when capturing the additional ultrasound acquisition using the ultrasound probe, a time duration of a button press to capture an identified location of the additional ultrasound acquisition indicates a relative depth of the portion of interest; and
after obtaining the 3D ultrasound image and obtaining the additional ultrasound acquisition,
generate first display data for display of the 3D ultrasound image;
receive a first user input;
in response to the first user input, generate second display data for replacing a portion of the 3D ultrasound image of the first display data with the additional ultrasound acquisition at the identified location of the additional ultrasound acquisition; and
display on the ultrasound image display the 3D ultrasound image with the additional ultrasound acquisition overlaying the 3D ultrasound image at the identified location of the additional ultrasound acquisition based on the second display data.

19. The system of claim 11, wherein the additional ultrasound acquisition comprises a 2D, contrast enhanced ultrasound image.

20. The system of claim 11, wherein the additional ultrasound acquisition comprises an ultrasound video.

* * * * *